United States Patent [19]

Nelson

[11] Patent Number: 4,596,252

[45] Date of Patent: Jun. 24, 1986

[54] PACER SENSE AMPLIFIER

[75] Inventor: Gary E. Nelson, Plymouth, Minn.

[73] Assignee: Medtronic, Inc., Minneapolis, Minn.

[21] Appl. No.: 730,417

[22] Filed: May 6, 1985

[51] Int. Cl.[4] .............................................. A61N 1/00
[52] U.S. Cl. ............................. 128/419 PG; 128/902
[58] Field of Search ................ 128/419 PG, 902, 696, 128/708; 330/109

[56]  References Cited

U.S. PATENT DOCUMENTS

| 4,459,996 | 7/1984 | Teele | 128/746 |
| 4,467,813 | 8/1984 | Schomburg | 128/902 |
| 4,494,551 | 1/1985 | Little, III et al. | 128/902 |
| 4,510,944 | 4/1985 | Porges | 128/687 |

*Primary Examiner*—William E. Kamm
*Assistant Examiner*—Mitchell J. Shein
*Attorney, Agent, or Firm*—Robert C. Beck; Joseph F. Breimayer; John L. Rooney

[57] ABSTRACT

A pacemaker sense amplifier circuit exhibiting a very high common mode rejection ratio for detecting intracardiac electrogram signals is disclosed. The circuit includes a sampling capacitor which is differentially charged by the intracardiac signal. The voltage stored on the sampling capacitor is periodically applied to a high input impedance differential voltage amplifier which is referenced to the battery ground. The signal is smoothed and reconstructed by a bandpass filter, and is applied to a comparator to generate a logic level pulse indicative of the occurrence of a cardiac depolarization.

1 Claim, 2 Drawing Figures

PACER SENSE AMPLIFIER

DESCRIPTION OF THE INVENTION

BACKGROUND OF THE INVENTION

Demand or VVI pacers are known from U.S. Pat. No. 3,057,356 to Wilson Greatbatch. Such pacers have a sense amplifier for detecting cardiac depolarizations in the ventricle of the heart. Upon the occurrence of a ventricular sense event, the pacer recycles and restarts the pacer's V-to-V timer circuitry. In the absence of a ventricular sense event, the pacer timer times out, generating a stimulation pulse which is applied to the heart.

In early pacers of the type taught by Greatbatch, the output pulse amplitude was on the order of 10 volts. More modern pacers, as typified by the teachings of U.S. Pat. No. 4,340,062 to McDonald, et al provide an output pulse amplitude which is programmable from approximately 1.5 volts to 5 volts. The sense amplifier circuits and timing circuits within a modern pacer operates from a supply voltage on the order of 2.8 volts which is the nominal open circuit potential of lithium chemistry batteries or cells. The programmable output voltages are derived from voltage divider and multiplier circuits associated with the output circuitry of the pacer.

The preceding pacers have only one sense amplifier coupled to the ventricular chamber of the heart, however, improved therapy may be achieved by pacers which sense and pace in both chambers of the heart. U.S. Pat. No. 4,312,355 to Funke is an example of a DDD or atrial and ventricular synchronized pacer which senses and paces in the atrium and the ventricle.

When dual chamber sensing is provided in a pacer with multiprogrammable output amplifiers reliable electrogram sensing becomes more difficult to achieve.

An output stimulus provided to one chamber of the heart is propagated throughout the heart and can induce a large potential difference on the sensing/pacing lead in the unstimulated chamber. Although the induced differential signal may be small, the common mode potential may be quite large and can on occasion exceed the nominal supply voltage of the battery.

Traditional sense amplifier circuitry suffers from reduced common mode rejection as the common mode voltage approaches the power supply rails. This can lead to false sensing by generating a false positive detection of the common mode signal or false negative detection through failure to trigger on a cardiac induced differential signal superimposed on a large common mode voltage. This problem is addressed by the present invention.

DETAILED DESCRIPTION OF THE PREFERRED EMBODIMENT

Figure 1:
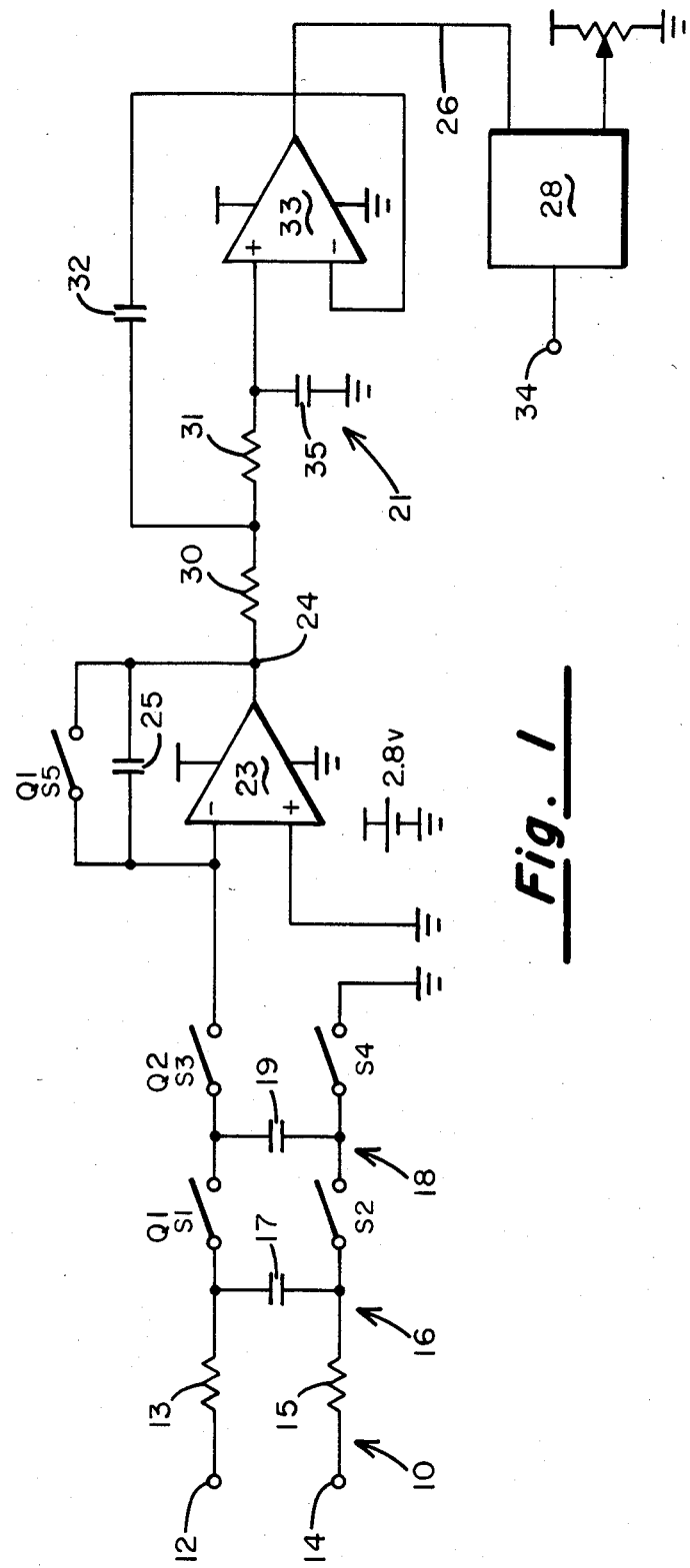
FIG. 1 depicts a sense amplifier circuit suitable for carrying out the invention.

FIG. 1 depicts a sense amplifier circuit suitable for carrying out the invention. The circuit is coupled to the heart through a lead system 10 which may include both tip 12 and ring 14 electrodes.

The lead system 10 applies the sensed signals to an analog or continuous time prefilter 16 exhibiting a low pass response with a half power bandwidth set equal to less than one half the sampling frequency. In the circuit topology shown, the resistors 13 and 15 provide DC coupling to the sampling network 18, while capacitor 17 provides an AC short between electrodes 12 and 14 as the input frequency increases beyond the filters corner frequency at a rate of 20 db/decade. This prefilter is required to ensure that the sampling network does not alias high frequency signals or noise into the sense amplifier passband.

Figure 2:
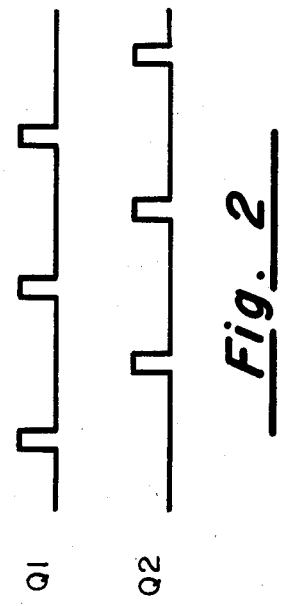
FIG. 2 depicts the timing pulses used in controlling the switches of FIG. 1.

The output of the anti-aliasing filter is coupled to the sampling network 18 which comprises clock controlled analog switches $S_1$-$S_4$. The switches are controlled by non-overlapping clock pulses $Q_1$ and $Q_2$ as shown in FIG. 2. The sampling frequency or clock frequency must exceed twice the highest frequency of interest within the sense amplifier passband. For a passband center frequency of 40 Hz, the sampling rate must be greater than 80 Hz and will typically be on the order of 1 KHz to provide good resolution of the input waveform and to ensure sufficient reduction of high frequency noise.

The sampling network connects the capacitor 19 to the lead system electrodes during the $Q_1$ clock phase. While the switches $S_1$ and $S_2$ are closed, 17 charges through a source impedance defined by resistors 13 and 15. On the negative going clock transition of $Q_1$, the switches $S_1$ and $S_2$ open and the charge on capacitor 19 is therefore retained or held. While the capacitor 19 is charging, the feedback capacitor 25 of operational amplifier 23 is shorted by switch $S_5$. This drives the inverting input of the op amp to battery ground potential. During the $Q_2$ clock phase, switches $S_3$ and $S_4$ close, coupling the capacitor 19 to battery ground, and the inverting input of operational amplifier 23. The amplifier 23 amplifies the differential voltage on 19 and provides a current source at the amplified voltage node 24. In this application, the amplifier 23 operates as a buffer presenting a high input impedance to the capacitor 19 and presenting a low impedance current source to the filter 21.

The output of the buffer at node 24 is coupled to a waveform recovery circuit 21. The function of this low pass smoothing filter is to reconstruct the input waveform; it has a corner frequency set at 40 Hz which is selected to pass the dominant frequency domain components of the intracardiac depolarization signal. The filter circuitry recovers and reproduces the original analog waveform. Component values listed on the figure give a Butterworth or maximally flat response. Other response curves such as Gaussian may be selected as alternatives.

The output of the low pass filter at node 26 is coupled to a bandpass filter and level detection circuit 28 to generate a logic compatible signal indicative of a cardiac depolarization. If sufficient energy is present in the passband of the filter 28, the output signal will toggle to generate the desired sense event signal.

Circuit values and components types for demonstrating the operation of the invention are included in Table 1.

TABLE 1

| | |
|---|---|
| R13 | 8k ohms |
| R15 | 8k ohms |
| R30 | 256k ohms |
| R31 | 256k ohms |
| C17 | .165 micro F |
| C19 | .01 micro F |

TABLE 1-continued

| | |
|---|---|
| C25 | .01 micro F |
| C32 | .022 micro F |
| C35 | .011 micro F |
| 23,33 | LF 356 H |
| $S_1$-$S_5$ | MC 140168 |

What is claimed is:

1. A pacer sense amplifier circuit for generating a logic level signal in response to sensed intracardiac electrograms (EKG) comprising:

a first electrode capable of being coupled to cardiac tissue, for receiving said EKG signals;

a second electrode capable of being coupled to cardiac tissue, for receiving said EKG signals;

an anti-aliasing filter coupled to said first electrode and said second electrode for defining the frequency domain response of said sense amplifier circuit;

a sampling capacity having first and second terminals;

a first pair of switches actuated in response to a first clock pulse for coupling said sampling capacitor to said anti-aliasing filter;

a buffer amplifier for presenting a high impedance load to said sampling capacitor and presenting a low impedance source to a waveform recovery circuit;

a second pair of switches actuated in response to a second clock pulse for coupling said sampling capacitor to said buffer amplifier;

a waveform recovery circuit coupled to said buffer amplifier for smoothing the sampled waveform to reconstruct the original EKG waveform;

a bandpass/level detector coupled to said waveform recovery circuit for generating a logic level signal whenever said recovered waveform generates sufficient energy within the passband of said detector, indicative of a cardiac depolarization.

* * * * *